(12) United States Patent
Giroud et al.

(10) Patent No.: US 11,337,627 B2
(45) Date of Patent: May 24, 2022

(54) BIOELECTRODE FOR DETECTION AND/OR OXIDATION OF GLUCOSE, ITS PRODUCTION METHOD AND DEVICE

(71) Applicants: CENTRE NATIONAL DE LA RECHERCHE SCIENTIFIQUE, Paris (FR); UNIVERSITE GRENOBLE ALPES, St Martin d'Heres (FR)

(72) Inventors: Fabien Giroud, Grenoble (FR); Andrew Gross, Grenoble (FR); Serge Cosnier, Crolles (FR)

(73) Assignees: CENTRE NATIONAL DE LA RECHERCHE SCIENTIFIQUE, Paris (FR); UNIVERSITE GRENOBLE ALPES, St Martin d'Heres (FR)

( * ) Notice: Subject to any disclaimer, the term of this patent is extended or adjusted under 35 U.S.C. 154(b) by 157 days.

(21) Appl. No.: 16/471,319

(22) PCT Filed: Dec. 19, 2017

(86) PCT No.: PCT/FR2017/053689
§ 371 (c)(1),
(2) Date: Jun. 19, 2019

(87) PCT Pub. No.: WO2018/115710
PCT Pub. Date: Jun. 28, 2018

(65) Prior Publication Data
US 2019/0328288 A1 Oct. 31, 2019

(30) Foreign Application Priority Data

Dec. 21, 2016 (FR) ...................................... 1662997

(51) Int. Cl.
| | |
|---|---|
| *A61B 5/1486* | (2006.01) |
| *A61B 5/145* | (2006.01) |
| *H01M 8/16* | (2006.01) |
| *C12N 11/02* | (2006.01) |
| *C12Q 1/00* | (2006.01) |
| *H01M 4/90* | (2006.01) |
| *C12N 11/06* | (2006.01) |
| *C12N 9/04* | (2006.01) |

(52) U.S. Cl.
CPC ........ *A61B 5/1486* (2013.01); *A61B 5/14532* (2013.01); *C12N 11/02* (2013.01); *H01M 8/16* (2013.01); *A61B 2562/0209* (2013.01); *C12N 9/0006* (2013.01); *C12N 11/06* (2013.01); *C12Q 1/006* (2013.01); *H01M 4/9008* (2013.01)

(58) Field of Classification Search
CPC ........................... C12N 9/0006; C12Y 101/05
See application file for complete search history.

(56) References Cited

U.S. PATENT DOCUMENTS

| | | | |
|---|---|---|---|
| 2004/0101741 A1* | 5/2004 | Minteer | ............... C12N 11/089 429/401 |
| 2009/0084678 A1 | 4/2009 | Joshi et al. | |
| 2014/0262830 A1 | 9/2014 | Cha et al. | |
| 2017/0335363 A1* | 11/2017 | Takahashi | ................ C12Q 1/54 |

OTHER PUBLICATIONS

Reuillard et al. "Non-covalent double functionalization of carbon nanotubes with a NADH oxidation Ru(II)-based molecular catalyst and a NAD-dependent glucose dehydrogenase" Chem. Commun., 50, 11731, 2014, (Year: 2014).*
Zor et al. "1,10-Phenanthroline-5,6-dione and 9,10-phenanthrenequinone as redox mediators for amperometric glucose biosensors" J Solid State Electrochem (2014) 18:1529-1536 (Year: 2014).*
Genys et al. "Electrochemical Deposition and Investigation of Poly-9,10-Phenanthrenequinone Layer" Nanomaterials 2019, 9, 702; (Year: 2019).*
Fapyane et al. "High performance enzyme fuel cells using a genetically expressed FAD-dependent glucose dehydrogenase a-subunit of Burkholderia cepacia immobilized in a carbon nanotube electrode for low glucose conditions" Phys.Chem. Chem. Phys., 2013, 15, 9508 (Year: 2013).*
International Search Report dated Mar. 19, 2018 issued in PCT/FR2017/053689.
Fapyane, Deby et al., "High performance enzyme fuel cells using a genetically expressed FAD-dependent glucose dehydrogenase a-subunit of Burkholderia cepacia immobilized in a carbon nanotube electrode for low glucose conditions", Phys. Chem. Chem. Phys. (2013), vol. 15, pp. 9508-9512.
Zafar et al., "Characterization of different FAD-dependent glucose dehydrogenases for possible use in glucose-based biosensors and biofuel cells", Anal Bioanal Chem (2012) 402:2069-2077.

\* cited by examiner

*Primary Examiner* — Thane Underdahl
(74) *Attorney, Agent, or Firm* — Scully, Scott, Murphy & Presser, P.C.

(57) ABSTRACT

The invention concerns a bioelectrode and a device comprising same, for detecting or oxidising glucose. The bioelectrode of the invention comprises a layer of carbon nano tubes to which aromatic molecules are bonded, and FAD-GDH enzymes being adsorbed on the aromatic molecules. The invention applies to the field of biosensors and biofuel cells in particular.

19 Claims, 3 Drawing Sheets

BIOELECTRODE FOR DETECTION AND/OR OXIDATION OF GLUCOSE, ITS PRODUCTION METHOD AND DEVICE

The invention is related to a bioelectrode based on flavin adenine dinucleotide glucose dehydrogenase, its uses for the detection or oxidation of glucose and devices comprising it, particularly a glucose detection device or an enzymatic biofuel cell for glucose oxidation.

It also relates to production methods for this bioelectrode.

Detection of glucose in urine or blood is important for detecting people with diabetes.

Thus, a glucose detection device is also important.

A glucose monitoring device that measures glucose levels in blood or urine of diabetic patients is a necessity for these patients to monitor their diabetes.

Such devices should ideally be easily transportable, i.e. small and light.

A large number of amperometric biosensors for detecting and quantifying glucose have been developed in recent years.

In addition, the rapid development of medical technology has recently made it possible to directly monitor and diagnose the performance of an organ in the body by implanted devices.

The energy supply of these devices by enzymatic biofuel cells is very promising, especially when the biofuel is glucose because in this case, the cell is constantly supplied with electrical energy from the glucose contained in the human physiological fluids.

Glucose detectors, like enzymatic biofuel cells supplying energy through glucose oxidation, use enzymes to act as catalysts that convert glucose into electrical energy.

As enzymes for detecting and/or oxidizing glucose, the Flavin Adenine Dinucleotide Glucose Dehydrogenase (FAD-GDH) enzymes were specifically studied and promoted in recent years.

The FAD-GDH is a thermostable enzyme which is highly selective at oxidizing glucose which does not use oxygen as an electron acceptor.

Zafar et al. in "Characterization of different FAD-dependent glucose dehydrogenases for possible use in glucose-based biosensors and biofuel cells", Anal Bioanal Chem (2012) 402: 2069-2077 describe an electrode consisting of a graphite rod on the top of which various ADF-GDH enzymes have been deposited and then cross-linked in a bone polymer.

However, such electrodes did not make it possible to obtain a high current density, thus showing that the electrical contact between the enzyme and the graphite was not sufficient.

The invention aims to overcome the problems of FAD-GDH electrodes of the prior art.

For this purpose, the invention proposes a bioelectrode characterized as the superposition of:
  a first layer of carbon nanotubes,
  a second layer, deposited on the first layer of carbon nanotubes, consisting of aromatic molecules chosen from the group formed by 9.10-phenanthrenequinone, 1.10-phenanthroline-5.6-dione, 9.10-anthraquinone, phenanthrene, 1.10-phenanthroline, 5-methyl-1.10-phenanthroline, pyrene, 1-aminopyrene, pyrene-1-butyric acid, and mixtures of two or more of these molecules,
  a third layer of flavin adenine dinucleotide glucose dehydrogenase (FAD-GDH) enzymes adsorbed on the second layer of aromatic molecules.

The bioelectrode of the invention may further comprise a fourth layer of a porous and/or hydrophilic material covering at least the free surface of the third layer of FAD-GDH enzymes.

This porous and/or hydrophilic material is preferably alginate, chitosan, Nation® or silica gel.

Preferably, in the bioelectrode according to the invention, the second layer of aromatic molecules consists of molecules of 9.10-phenanthrenequinone or 1.10-phenanthroline-5.6-dione.

Also preferably, in the bioelectrode according to the invention, the layer of carbon nanotubes consists of between 2.5 µg and 510 µg of carbon nanotubes per $cm^2$ of layer surface, preferably between 2.5 and 100 µg of carbon nanotubes, carbon per $cm^2$ of surface of the first layer of carbon nanotubes.

In a first embodiment, the bioelectrode of the invention consists also of a support made of an electrically conductive material, preferably vitreous carbon, under the first layer of carbon nanotubes.

Even more preferably, the bioelectrode of the invention also consists of a wire made of an electrically conductive material connected to the surface of the layer of carbon nanotubes which is not covered with the second layer of aromatic molecules.

Copper, silver copper, or platinum is usually used as electrically conductive material.

In the bioelectrode of the invention, the conductive wire is preferably silver-plated copper.

In a second embodiment of the bioelectrode of the invention, the bioelectrode of the invention further consists of a fluid-impermeable coating layer, preferably a silicone-based polymer, deposited on the free surfaces of the layers of carbon nanotubes and enzymes and on the edges of the superposition of the first, second and third layers of carbon nanotubes, aromatic molecules and FAD-GDH enzymes.

The invention also proposes a device consisting of a bioelectrode according to the invention.

This device can be an enzymatic biofuel cell.

This device can also be a glucose detector when the coating layer is not present.

The invention also proposes the use of a bioelectrode according to the invention or a device according to the invention for the oxidation of glucose.

The invention also proposes a first production method for a bioelectrode according to the invention, characterized as the following steps:
  a) preparing a suspension with a concentration of between 0.5 mg·$mL^{-1}$ and 10 mg·$mL^{-1}$, and preferably 2.5 mg·$mL^{-1}$ of carbon nanotubes in an organic solvent, preferably selected from 1-methyl-2-pyrrolidinone (NMP), dichloromethane (DCM), acetonitrile (ACN), 1.3-dioxolane (DXL), dimethylformamide (DMF)), and mixtures of two or more of these molecules preferably NMP,
  b) depositing a drop (drop-casting) of the suspension of carbon nanotubes obtained in step a) on a support made of an electron-conducting material, preferably glassy carbon,
  c) evaporating the organic solvent from the suspension of carbon nanotubes, whereby a layer of carbon nanotubes is formed on the support,
  d) preparing a solution consisting of aromatic molecules selected from the group consisting of 9.10-phenanthrenequinone, 1.10-phenanthroline-5.6-dione, 9.10-anthraquinone, phenanthrene, 1.10-phenanthroline, 5-methyl-1.10-phenanthroline, pyrene, 1-aminopyrene, 1-pyrene-butyric acid, and mixtures of two or more aromatic molecules, with having a concentration between 0.5 mmol·$L^{-1}$ to 15 mmol·L$^{-1}$, and preferably 2.5 mmol·L$^{-1}$, dissolved in an organic solvent selected from NMP, DCM, ACN, DXL, DMF, and mixtures of two or more molecules, preferably ACN, identical to or different from the organic solvent of the carbon nanotube suspension, e) depositing on a surface of nanotube carbon layer obtained in step c), the solution of aromatic molecules obtained in step d), by depositing a drop (drop-casting) of the solution of aromatic molecules on the surface of the layer of carbon nanotubes or by incubation of at least the free surface of the layer of carbon nanotubes in the solution of aromatic molecules obtained in step d), the drop-casting or the solution of incubation preferably with a volume of between 5 and 200 µl, where more preferably the volume is 175 µl, f) evaporating the solvent from the solution of aromatic molecules deposited in step e), whereby a layer of aromatic molecules is formed on the layer of carbon nanotubes, g) preparing an aqueous solution of FAD-GDH enzymes preferably with a concentration of FAD-GDH enzymes between 0.1 mg·mL$^{-1}$ and 5 mg·mL$^{-1}$, and preferably 0.75 mg mL$^{-1}$ of FAD-GDH enzymes, h) depositing on the layer of aromatic molecules obtained in step f), the FAD-GDH enzyme solution obtained in step g), by incubation of at least the free surface of the layer of aromatic molecules obtained in step f), in an aqueous solution containing the FAD-GDH enzymes obtained in step g), or by depositing a drop (drop-casting) of said aqueous solution containing the FAD-GDH enzymes obtained at step g) on the free surface of the layer of aromatic molecules. The volume of enzyme solution used for the incubation or the drop of enzyme solution is preferably between 5 and 200 µL, more preferably 40 µL, In this first method, preferably step a) related to depositing a drop of the dispersion of carbon nanotubes is repeated at least once.

The invention also proposes a second production method for a bioelectrode according to the invention, characterized in that it comprises the following steps:

A) preparing a volume of 150 ml of a suspension of carbon nanotubes in an organic solvent preferably selected from NMP, DCM, ACN, DXL, DMF, and mixtures of two or more of these, preferably DMF, where the suspension has a carbon nanotube concentration of between 1 mg·mL$^{-1}$ and 15 mg·mL$^{-1}$, and preferably 1 mg·mL$^{-1}$, B) preparing a 5 mL solution containing 0.3 mmol of aromatic molecules selected from the group consisting of 9.10-phenanthrenequinone, 1.10-phenanthroline-5.6-dione, 9.10-anthraquinone, phenanthrene, 1.10-phenanthroline, 5-methyl-1.10-phenanthroline, pyrene, 1-aminopyrene, pyrene-1-butyric acid, and mixtures of two or more of the molecules, preferably 1.10-phenanthroline-5.6-dione, in an organic solvent identical to or different from the organic solvent of the suspension of carbon nanotubes obtained in step a), preferably DMF, C) adding the 5 ml of the solution of aromatic molecules obtained in step B) into the 150 ml of the suspension of nanotubes obtained in step A), and mixing the suspension obtained, D) filtering the dispersion obtained in step C) through a filter support, E) evaporating the solvent from the suspension of carbon nanotubes and the solvent of the solution of aromatic molecules, whereby a layer of carbon nanotubes is itself covered on at least one of its surfaces with a layer of said aromatic molecules are formed, F) preparing an aqueous solution of FAD-GDH enzymes with a concentration of FAD-GDH enzymes of between 0.1 and 5 mg·mL$^{-1}$, preferably 0.75 mg·mL$^{-1}$, G) drop-casting deposit of 150 µL of the FAD-GDH enzyme solution prepared in step F) on the free surface of the layer of aromatic molecules thus forming a layer of FAD-GDH enzymes adsorbed on the layer of aromatic molecules, H) removing the assembly obtained in step G) of the filter support.

The invention also proposes a production method for a bioelectrode according to the invention, characterized in that it comprises the following steps:

a1) preparing a 150 mL volume of a suspension of carbon nanotubes in an organic solvent selected from NMP, DCM, ACN, DXL, DMF, and mixtures of two or more molecules preferably DMF, where the suspension has a concentration of carbon nanotubes of between 1 mg·mL$^{-1}$ and 15 mg·mL$^{-1}$, preferably 1 mg·mL$^{-1}$, b1) preparing a solution of aromatic molecules with a concentration of between 0.1 mmol·L$^{-1}$ and 10 mmol·L$^{-1}$, preferably 10 mmol·L$^{-1}$ and selected from the group consisting of 9.10-phenanthrenequinone, 1.10-phenanthroline-5.6-dione, 9.10-anthraquinone, phenanthrene, 1.10-phenanthroline, 5-methyl-1.10-phenanthroline, pyrene, 1-aminopyrene, pyrene-1-butyric acid, and mixtures of two or more molecules, preferably 1.10-phenanthroline-5,6-dione, in an organic solvent selected from NMP, DCM, ACN, DXL, DMF, and mixtures of two or more molecules identical to or different from the organic solvent of the carbon nanotube suspension obtained in step a1), preferably DMF, c1) filtering the dispersion obtained in step a1) through a filter support, d1) evaporating the solvent from the dispersion of carbon nanotubes deposited in step c1) whereby a layer of carbon nanotubes is formed, e1) removing the layer of carbon nanotubes obtained in step d1) of the filtering support, f1) deposit by drop-casting of 150 µL of the solution of aromatic molecules obtained in step b1) on at least one surface of the layer of carbon nanotubes obtained in step e1), or by soaking the layer of carbon nanotubes obtained in step e1) in the solution prepared in b1).

g1) evaporating the solvent from the solution of aromatic molecules deposited in step f1), whereby a layer of said aromatic molecules is formed on the layer of carbon nanotubes, h1) preparing an aqueous solution of FAD-GDH enzymes with a concentration of FAD-GDH enzymes of between 0.1 and 5 mg·mL$^{-1}$, i1) deposit by drop-casting of 150 µL of the solution or by soaking the layer of carbon nanotubes obtained in step g1) in the solution prepared in h1) of FAD-GDH enzymes obtained in step h1) on the layer of aromatic molecules, thus forming a layer of FAD-GDH enzymes adsorbed on the layer (3).

Preferably, the second and third methods of the invention further comprise a step k1) of fastening a wire made of an electrically conductive material, preferably a material selected from copper, silver copper, platinum, more preferably silver copper, on the surface of the layer of carbon nanotubes not covered by the aromatic molecule layer, where this step is carried out before or after step G) or i1) of depositing the layer of FAD-GDH enzymes.

Preferably, all the production methods for a bioelectrode according to the invention also comprise a step of coating the superposition: layer of carbon nanotubes/layer of aromatic molecules/layer of FAD-GDH enzymes/wire made of electrically conductive material, preferably with a silicone-based compound.

The invention will be better understood and other characteristics and advantages thereof will appear more clearly on reading the explanatory description which follows and which is made with reference to the figures in which.

Figure 1:
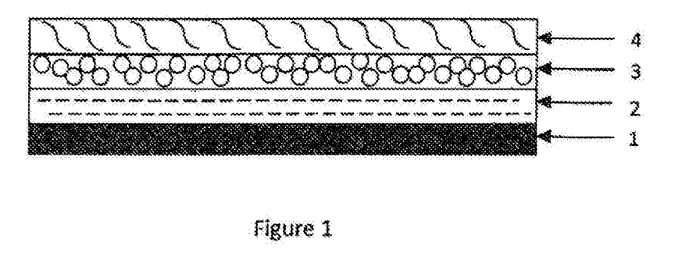
FIG. 1 shows a first embodiment of the electrode of the invention, described in example 1.

As shown in FIG. 1, in a first embodiment, the bioelectrode of the invention consisting of the superposition on a conducting support, denoted 1 in FIG. 1, of a layer, denoted 2 in FIG. 1, of carbon nanotubes, on which a layer is deposited, denoted 3 in FIG. 1, of aromatic molecules, on which a layer is deposited, denoted 4 in FIG. 1, of Flavine Adenine Dinucleotide-Glucose Dehydrogenase (FAD-GDH) enzymes.

In the invention, carbon nanotube means a carbon nanotube of which at least one dimension is less than 1500 nm.

Layer 2 of carbon nanotubes may consist of single-walled or multi-walled carbon nanotubes.

However, preferably, it consists of multi-walled carbon nanotubes.

In fact, the multi-wall carbon nanotubes have a larger external diameter and therefore a higher developed surface, which makes it possible to better immobilize the aromatic molecules and the enzymes.

Preferably, the carbon nanotubes have a length (L) to diameter ratio denoted by L/diameter of between 100 and 5000.

Preferably, the carbon nanotubes have a length of 1.5 µm and an internal diameter of 9.5 nm.

Layer 2 of carbon nanotubes must be porous.

The pore size in layer 2 of carbon nanotubes must be more than 8 nm, the size of the FAD-GDH enzyme is of 78 Å (7.8 nm).

Preferably, the pore size of layer 2 of carbon nanotubes is between 8 and 50 nm.

More preferably, the pore size of the layer of carbon nanotubes is 10 nm. The aromatic molecules forming layer 3 are linked by interaction π-π on layer 2 of carbon nanotubes.

Although in FIG. 1 (as in FIGS. 2 and 3), layer 2 of carbon nanotubes and layer 3 of aromatic molecules are represented as a true superposition, the person skilled in the art will readily understand that layer 2 consists of porous carbon nanotubes which are themselves made up of several "sub-layers" of carbon nanotubes, the aromatic molecules also bind to carbon nanotubes (sublayers).

Figure 2:
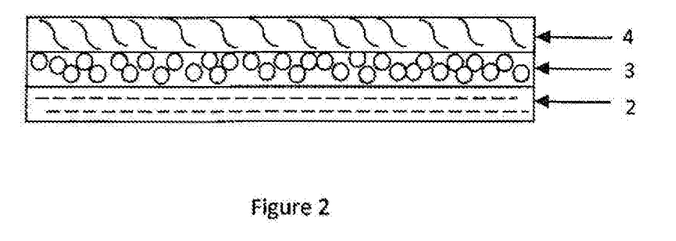
FIG. 2 shows a second embodiment of the electrode of the invention, described in example 2.
Figure 3:
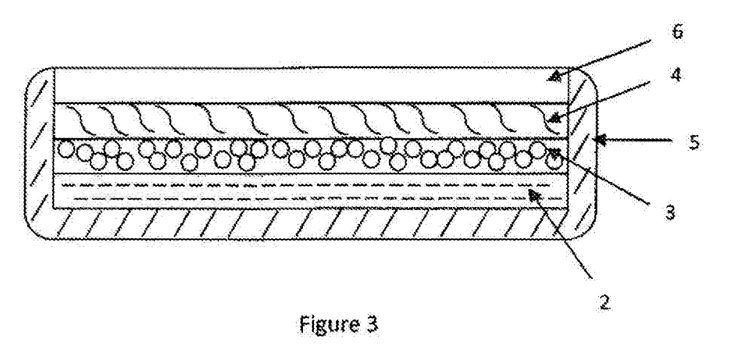
FIG. 3 shows a third embodiment of the electrode of the invention, described in example 3.

Thus, the layers 2 and 3 are not individualized but imbricated one inside the other.

Aromatic molecules promote the transfer of electrons between the enzyme and carbon nanotubes.

Furthermore, they play the role of molecules orienting the three-dimensional structure of the enzyme which will then be adsorbed on these molecules so as to promote the electronic transfer of the enzyme to the carbon nanotubes.

The aromatic molecules forming layer 3 are chosen from 9.10-phenanthrenequinone, 1.10-phenanthroline-5.6-dione, 9.10-anthraquinone, phenanthrene, 1.10-phenanthroline, 5-methyl-1.10-phenanthroline, pyrene, 1-aminopyrene, pyrene-1-butyric acid, and mixtures of two or more of these molecules.

Preferably, the aromatic molecules forming layer 3 are molecules phenanthrene or 1.10-phenanthroline-5.6-dione.

And it is particularly surprising that such aromatic molecules can mediate between the carbon nanotubes and the FAD-GDH enzyme because, in particular, the 1.10-phenanthroline molecule is known to be an inhibitor of the enzyme FAD-GDH, for the oxidation of glucose because it takes the place of glucose in this oxidation reaction.

The inhibitory activity of 1.10-phenanthroline for the reaction of FAD-GDH is emphasized by the companies marketing this enzyme, see for example Sekisui Enzymes, "Glucose Dehydrogenase FAD Dependent, Catalog No. GLDE-70-1192, EC number 1.1.99.10".

This inhibitory activity for the 9.10-phenanthrenequinone, 1.10-phenanthroline-5.6-dione, phenanthrene and 1.10-phenanthroline molecules was confirmed by cyclic voltammetric assays.

Figure 5:
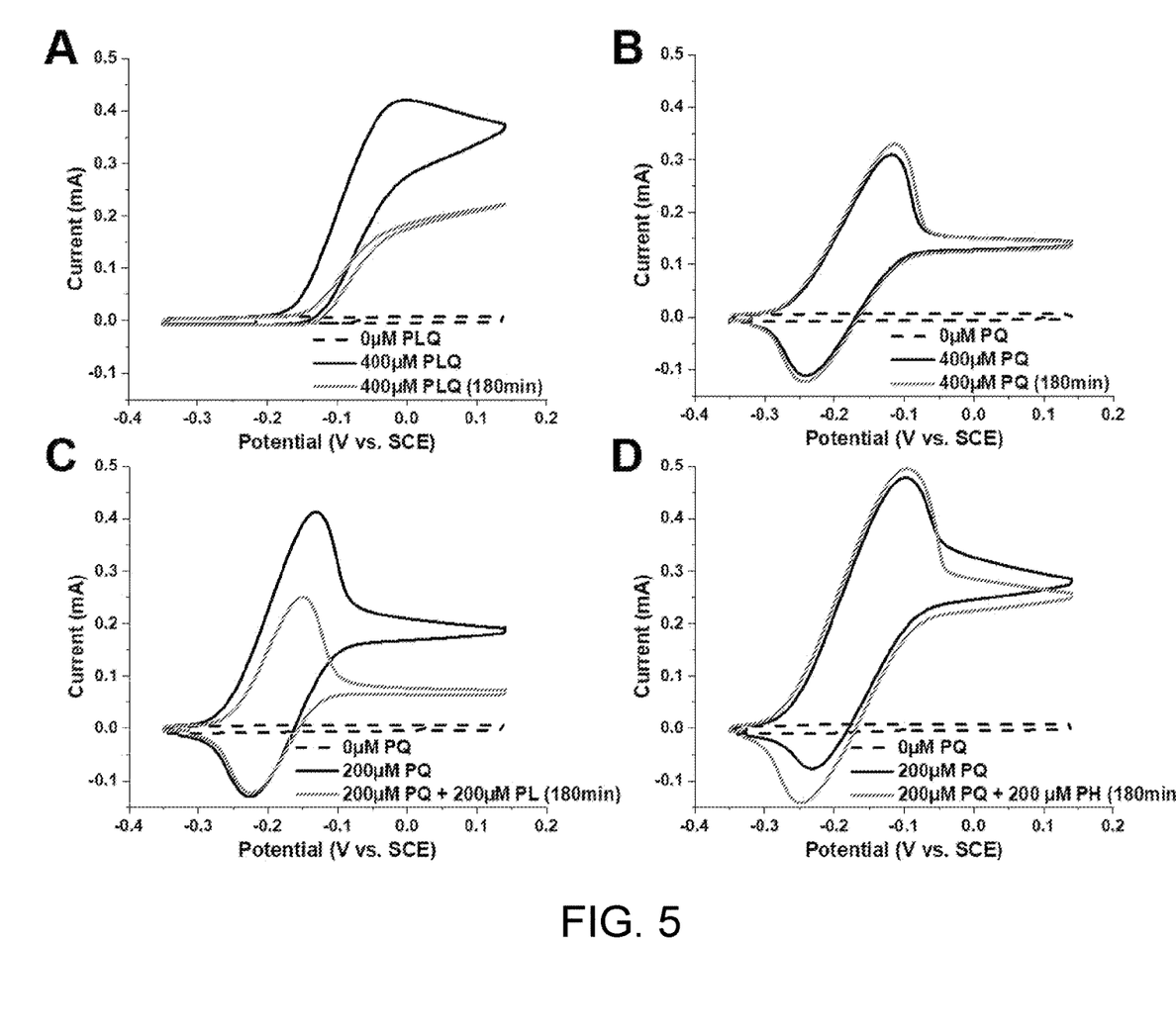
FIG. 5 shows the voltammograms obtained with the electrodes obtained in example 13.

The voltammograms obtained during these tests are shown in FIG. 5. They were obtained with electrodes whose layer of FAD-GDH enzymes is directly deposited on layer 2 of carbon nanotubes in the presence of 100 mmol $L^{-1}$ of glucose solution.

The aromatic molecules 9.10-phenanthrenequinone, 1.10-phenanthroline-5.6-dione, phenanthrene and 1.10-phenanthroline are then gradually added in solution.

The presence of 200 µmol $L^{-1}$ of 9.10-phenanthrenequinone or phenanthrene does not cause a drastic decrease in the catalytic currents measured for sampling times of less than three hours.

On the other hand, the presence of aromatic molecule based on pyridines such as 1.10-phenanthroline-5.6-dione and 1.10-phenanthroline generates a progressive decrease in the performance of bioelectrocatalysis over time.

The layer of FAD-GDH enzymes, denoted 4 in FIGS. 1 to 3, is a layer of functionalization of the aromatic molecules of the layer denoted 3 in FIGS. 1 to 3.

The enzyme or enzymes forming layer 4 are (are) adsorbed on the aromatic molecules forming layer 3.

Here again, although in FIG. 1 (as in FIGS. 2 and 3), layer 4 of FAD-GDH enzymes is represented as a distinct layer in contact only with layer 3 of aromatic molecules, the person skilled in the art will readily understand that the FAD-GDH enzymes constituting layer 4 are also adsorbed on the organic molecules which are themselves bound (by π-π bond) to the carbon nanotubes present in the sub-layers of layer 2 of carbon nanotubes.

In other words, the superposition of layers 2, 3 and 4 is actually made up of individual carbon nanotube-aromatic molecule-FAD-GDH enzyme assemblies.

In this first embodiment, preferably, the amount of carbon nanotubes deposited on the surface of the support 1 is between 2.5 µg of carbon nanotubes per $cm^2$ of surface of the substrate 1 and 510 µg of carbon nanotubes per $cm^2$ of the surface of the support 1, for an application of the electrode in a glucose sensor and is between 5 µg and 100 µg of carbon nanotubes per $cm^2$ of support surface 1 when the electrode is intended to be used as an electrode of a biofuel cell for the oxidation of glucose.

In fact, in such an application, if the amount of carbon nanotubes per $cm^2$ of support surface is less than 5 µg, there is not enough carbon nanotubes to produce a catalytic stream that allows the biotech battery to provide sufficient electrical energy and when the amount of carbon nanotubes is more than 100 µg per cm² of support surface 1, layer 2 of carbon nanotubes is formed of several sub-layers of carbon nanotubes stacked up one on the other and the inner layers (those that are not on the surface) of carbon nanotubes do not see a lower concentration of glucose since it is oxidized mainly in the upper layers.

In this first embodiment of the invention the electrode is an electrode supported on a support denoted 1 in FIG. 1.

But, in a second embodiment shown in FIG. 2, the bioelectrode of the invention is self-supported.

The superposition of layers 2, 3 and 4 as described in the first embodiment is then performed on a surface of this support 1.

The support 1 is made of an electronically conductive material, preferably vitreous carbon.

In the second embodiment of the bioelectrode of the invention, it further consists of a conductive wire of an electrically conductive material for transferring the current of the electrode to the glucose detection or oxidation device.

In all the embodiments of the bioelectrode of the invention, and as shown in FIG. 3, at least the free surface of the layer of FAD-GDH enzymes 4 is protected by a layer denoted 6, in FIG. 3 porous and/or hydrophilic material.

This layer 6 has a role of protecting FAD-GDH enzymes by preventing the displacement of FAD-GDH enzymes in the environment in which the bioelectrode of the invention is intended to be used.

This layer 6 must be made of a porous material to allow access of the glucose-containing fluid to the FAD-GDH enzymes and to the displacement of oxidation reaction products (gluconolactone and protons), while not letting the FAD-GDH enzymes pass through.

Therefore, the pore diameter of the material constituting layer 6 must be less than 78 Å. It is preferably less than 75 Å. This makes it possible to encapsulate the enzyme on the electrode while ensuring the diffusion of the substrate and the product to and from the electrode respectively.

The material constituting layer 6 is preferably hydrophilic, too, to improve the displacement in the bioelectrode of the aqueous medium in which it will be placed.

Preferably, layer 6 is alginate, or chitosan, or Nafion® or silica gel.

Layer 6 preferably covers the entire bioelectrode.

However, when a coating layer 5 of a fluid-impermeable material is provided, only the surface of layer 4 must imperatively be covered with layer 6.

Indeed, when the bioelectrode of the invention is intended to be placed in a biocell for glucose oxidation, it is preferably coated, as shown in FIG. 3, in a layer of a material impermeable to fluids thus forming a coating layer, denoted 5 in FIG. 3.

This coating layer 5 must not cover layer 6.

Layer 5 is made of a fluid-impermeable material, preferably a silicone material.

This layer 5 makes it possible to ensure the stability of the superposition of layers constituting the bioelectrode of the invention and to prevent the displacement of carbon nanotubes, aromatic molecules and FAD-GDH enzymes in which the bioelectrode of the invention is to be placed.

This layer 5 is particularly important when layer 6 does not cover the set of superposition of layers 2, 3, and 4 and possibly support 1.

The invention also proposes a device consisting of a bioelectrode according to the invention.

This device can be a biofuel cell in which the energy is produced by the oxidation of glucose.

Indeed, the bioelectrode of the invention is very small and very light and can be placed in a miniaturized portable device or implanted directly in the body of a human or an animal.

This device can also be a device for detecting and quantifying glucose in a human body fluid such as blood, urine, tears or sweat. In this case, the bioelectrode is not embedded in layer 5 but completely covered with layer 6.

The bioelectrode of the invention can be produced by very simple methods which do not implement any chemical reaction or synthesis step of creation of active redox polymers or complicated supra-molecular assemblies.

In addition, with the methods of the invention, the thicknesses of the bioelectrodes and the amounts of meadiatric aromatic molecules and enzymes can be modified according to the sensitivity and efficiency required for the intended application of these bioelectrodes.

A first production method for the bioelectrode according to the invention is a production method for a bioelectrode supported on a rigid support 1.

The support 1 is made of an electrically conductive material, preferably vitreous carbon.

This method comprises, as all the other methods according to the invention: a step of preparing a suspension of carbon nanotubes in an organic solvent.

As an organic solvent usable for this slurry includes NMP, DCM, ACN, DMF DXL and mixtures of two or more thereof.

The preferred organic solvent is NMP because this solvent has a better affinity (wettability) with the support 1, when the latter is glassy carbon.

The suspension should have a concentration of carbon nanotubes for depositing, in the form of a drop (so-called "drop-casting" method) a quantity of carbon nanotubes of between 2.5 µg and 510 µg per cm² of support 1 area, when the bioelectrode of the invention is to be used in a glucose sensor.

Generally a concentration between 0.5 mg·mL$^{-1}$ and 10 mg·mL$^{-1}$ is used. If the concentration of carbon nanotubes in the dispersion is too high, the layers of carbon nanotubes obtained are less stable and less reproducible because of a less good dispersion in the solution.

Preferably a concentration of 2.5 mg·mL$^{-1}$ is used.

The quantity of nanotubes deposited on the support 1 is preferably between 5 µg and 100 µg of carbon nanotubes per cm² of support surface when the bioelectrode is intended to be used to produce a biofuel cell.

Indeed, in this case, the amount of carbon nanotubes is less than 5 µg per cm² of support surface, and there is not enough carbon nanotubes to provide a catalytic current that allows the battery to provide more power.

Put more than 100 µg per cm² of surface of the support, the thickness of this layer is then important and the carbon nanotubes which are under the other carbon nanotubes do not "serve" for the oxidation of glucose because the glucose present in the fluid is oxidized by the nanotubes on the surface of the support; the glucose no longer diffuses throughout the layer formed by the nanotubes.

Then, as for all the methods of the invention, this first method of the invention consists of solution preparation phase of the desired aromatic molecule (s) by dissolving this (these) aromatic molecule (s) in an organic solvent. The solvent may be the same as or different from the organic solvent of the carbon nanotube suspension.

Thus, a usable organic solvent to dissolve organic molecules include NMP, DCM, ACN, DXL, DMF and mixtures of two or more molecules.

However, preferably, the organic solvent for dissolving the aromatic molecule or molecules is identical to the organic solvent used for suspending the carbon nanotubes.

As such, it is also preferably NMP in the first method of the invention.

The concentration of organic molecules in the solution is preferably between 0.5 mmol $L^{-1}$ 15 mmol $L^{-1}$. It is preferably 2.5 mmol $L^{-1}$.

The first method of the invention, like all the methods of the invention, consists of a solution preparation phase of an aqueous solution of FAD-GDH enzymes as well.

Aqueous solution means a buffer solution of pH between 4.0 and 9.0. The buffer solutions that can be used and their water proportions are based on citric acid, acetic acid, phosphate, any other species likely to act as a buffer or mixtures of two or more of these elements to keep pHs between 4.0 and 9.0.

The concentration FAD-GDH enzyme in this aqueous solution is preferably between 0.1 mg·$mL^{-1}$ and 5 mg·$mL^{-1}$. It is more preferably 0.75 mg·$mL^{-1}$.

Once the suspension of carbon nanotubes is prepared, in the first production method for the bioelectrode of the invention, a drop of a maximum volume of 20 μL of the carbon nanotube dispersion is deposited on a surface of the support 1.

Indeed, if the drop volume deposited is greater, the thickness of the layer of carbon nanotubes is increased and could be detrimental to the diffusion of glucose in the porous layer.

It is possible to repeat this step more than one time to increase the amount of deposited carbon nanotubes and thus increase the specific active surface area of the bioelectrode.

Once the formation of a layer 2 of carbon nanotubes of the desired thickness has been obtained, the solution of aromatic molecules is brought into contact with this layer of carbon nanotubes, generally at ambient temperature (between 15 and 30° C.).

This contacting can be carried out by incubation of the support assembly 1 covered with layer 2 of carbon nanotubes in the solution of aromatic molecules or only the free surface of layer 2 of carbon nanotubes by deposition of a drop of the solution of aromatic molecules directly on the layer of carbon nanotubes.

The solution of aromatic molecules is left in contact with layer 2 of carbon nanotubes for a time period between 5 minutes and 1 hour to allow functionalization of the carbon nanotubes.

The adsorption of more aromatic molecules cannot be done within a period of more than one hour.

Then the assembly of the support 1/layer 2 of carbon nanotubes/layer 3 of aromatic molecules in solution is rinsed with distilled water to remove the aromatic molecules which would be adsorbed only slightly on the carbon nanotubes of layer 2.

Indeed, the aromatic molecules are adsorbed on the carbon nanotubes by a π-π interaction and thus form a layer 3 of aromatic molecules.

Then, the assembly support 1/layer of carbon nanotubes 2/layer 3 of aromatic molecules is contacted with the aqueous solution containing FAD-GDH enzymes for a sufficient period of time for the preferred orientation of the FAD-GDH enzyme versus organic molecules.

Generally, a time varying from 4 hours to 1 day at 4° C. is used.

The FAD-GDH aqueous enzyme solution is a buffered solution at a pH of between 4.0 and 9.0 and preferably a pH of 7.0 to avoid damaging the enzyme FAD-GDH.

Finally, the bioelectrode thus obtained is thoroughly rinsed with the buffered solution (still so as not to damage the enzyme FAD-GDH) to remove the adsorbed enzymes loosely thus forming a layer 4 of FAD-GDH enzyme.

If the bioelectrode thus obtained is not used immediately, it is stored in a buffer solution or in air until use or reuse.

A second method for producing a bioelectrode according to the invention is a method in which the bioelectrode is self-supporting, in other words, it does not comprise a support 1.

In this second method, once the suspension of carbon nanotubes and the FAD-GDH solutions of molecules and enzymes have been prepared, the solution of aromatic molecules is added to the suspension of carbon nanotubes and the solution obtained is generally treated with ultrasound for 30 minutes.

In the second method of the invention, the suspension of carbon nanotubes has a concentration of between 1 mg·$mL^{-1}$ and 15 mg·$mL^{-1}$, and preferably 1 mg·$mL^{-1}$.

This mixed dispersion of carbon nanotubes-aromatic molecules is then filtered under vacuum on a filter made of a chemically inert polymer material.

Such a chemically inert polymer material is preferably polytetrafluoroethylene (PTFE).

Thus, what is called "Buckypaper" was formed from the art.

This "Buckypaper" is removed from the filter and left to dry flat, usually overnight at room temperature. It is then cut to the desired size.

Then, this "Buckypaper" is incubated in, or is covered with a drop, of buffered aqueous solution of FAD-GDH enzymes for between 4 hours and 1 day, preferably overnight, at 4° C.

After this period of incubation or keeping in contact, the "Buckypaper" is rinsed with a buffer solution to remove the enzymes adsorbed loosely on the surface of the aromatic molecules. Buffer solutions that can be used as well as their proportions in water are based on citric acid, acetic acid, phosphate, any other species likely to act as a buffer or mixtures of two or more of these elements to keep pHs between 4.0 and 9.0.

To ensure the electrical connection of the electrode, a wire is attached to the back of the electrode for example with a carbon paste followed by the application of a silicone material.

This step of attaching the wire may be performed before or after the formation of layer 4 of FAD-GDH enzymes.

The third method of the invention also consists in preparing a "Buckypaper", but this time only consisting of carbon nanotubes.

Thus, the difference between the second method and the third method of the invention is that the suspension of carbon nanotubes is not mixed with the solution of aromatic molecules before being deposited on a filter support but it is deposited alone on the filter support.

Then the solvent of carbon nanotube suspension is filtered and the layer of carbon nanotubes is removed from the filter support: a "Buckypaper" was formed consisting solely of carbon nanotubes.

Then, the solution of aromatic molecules is deposited by "drop-casting" on this layer of carbon nanotubes, as in the first method of the invention.

The first method of the invention is then followed.

In order to improve the understanding of the invention, several examples of its implementation will now be described, for illustrative and non-limiting purposes only.

EXAMPLE 1: PRODUCTION OF A BIOELECTRODE ACCORDING TO THE INVENTION SUPPORTED ON A GLASSY CARBON SUPPORT

This example will be described with reference to appended FIG. 2.

A suspension of multi-walled carbon nanotubes (9.5 nm in diameter, purity of more than 95%) is obtained from non-functionalized carbon nanotubes by ultrasound treatment in NMP for 30 minutes.

The concentration of carbon nanotubes of this suspension is 2.5 mg·mL$^{-1}$.

The dispersion is stable and is vigorously shaken to improve the reproducibility of the deposition of the layer of carbon nanotubes on the support 1.

A drop of a volume of 20 μL of this suspension is deposited on the surface of the support 1 in vitreous carbon.

The NMP is then evaporated under support vacuum (vacuum$_{max}$=10$^{-3}$ mbar).

The support 1 in vitreous carbon coated on one of its surfaces is obtained with a layer 2 of dry carbon nanotubes.

This assembly is then incubated in a solution of 1.10-phenanthroline-5.6-dione at a concentration of 2.5 mmol·L$^{-1}$ in ACN for one hour at room temperature.

The assembly thus obtained is then rinsed thoroughly with distilled water to remove the 1.10-phenanthroline-5.6-dione molecules not completely bound to the carbon nanotubes of layer 2.

At this stage, a support assembly 1/layer 2 of carbon nanotubes/layer 3 of 1.10-phenanthroline-5.6-dione molecules is then obtained.

A drop of 40 μl of FAD-GDH enzyme solution buffered to pH 7.0 and having a concentration of 0.75 mg·mL$^{-1}$ of enzymes is then deposited on the surface of the assembly obtained from the three layers 1, 2 and 3.

This assembly is then left overnight at 4° C. for adsorption of the enzymes.

Finally, the assembly obtained is thoroughly rinsed with a McIlvaine buffer solution (0.2 mol L$^{-1}$ Na$_2$HPO$_4$, 0.1 mol L$^{-1}$ citric acid) buffered at pH 7.0 to eliminate the enzymes adsorbed in a loose manner on the surface of the molecules of 1.10-phenanthroline-5.6-dione.

EXAMPLE 2: PRODUCTION OF A BIOELECTRODE ACCORDING TO THE SELF-SUPPORTED INVENTION ("BUCKYPAPER" ELECTRODE)

A suspension of multi-walled carbon nanotubes in DMF is prepared by adding 150 mg of non-functionalized multi-walled carbon nanotubes (9.5 nm in diameter, purity of more than 95%) in 150 ml of DMF.

The suspension obtained has a concentration of carbon nanotubes of 1 mg·mL$^{-1}$.

The dispersion is then sonicated for 30 minutes.

A solution of 1.10-phenanthroline-5.6-dione molecules is then prepared by dissolving 65 mg of solid in a volume of 5 ml of DMF and slowly added to the suspension of multi-walled carbon nanotubes to a final molecule concentration of 1.10-phenanthroline-5.6-dione of 2 mmol L$^{-1}$.

The resulting suspension is then sonicated for another 30 minutes.

After vigorous manual stirring for one minute, 66 mL of the suspension thus obtained is filtered through a PTFE millipore filter (JHWP 0.45 μm pore size, 46 mm in diameter) using a vacuum pump (Vacuum$_{Max.}$=10$^{-3}$ mbar). The whole is washed with distilled water and allowed to stand for one hour.

Then, the assembly of layer 2 of carbon nanotubes/layer 3 of aromatic molecules is removed from the filter support and cut into an electrode precursor of 10 mm diameter (geometric specific surface of 0.785 cm$^2$).

An electrical contact is obtained via a wire held by a carbon paste (Acheson, ELECTRODAG 423 SS) on the free surface of layer 2 of carbon nanotubes of the assembly obtained.

Then 150 μL of a FAD-GDH enzyme solution are deposited on the surface of the assembly of layer 2 of carbon nanotubes/layer 3 of 1.10-phenanthroline-5.6-dione molecules.

The solution of FAD-GDH enzymes is a 5 mg·mL$^{-1}$ solution of FAD-GDH enzymes prepared in a McIlvaine buffer pH 7.0 (0.2 mol·L$^{-1}$ Na$_2$ HPO$_4$, 0.1 mol L$^{-1}$ citric acid).

The assembly is placed in the refrigerator (4° C.) overnight and then rinsed with the buffer solution.

Then, the other side of the bioelectrode and its sides are sealed with a silicone paste (manufacturers: Rubson, GEB) to form a coating layer 5.

EXAMPLE 3

The same method as in Example 2 was followed, but the assembly was also encapsulated in a coating layer 6.

This layer may be alginate, chitosan, Nafion®' or silica gel, for example.

The electrode shown in FIG. 3 was obtained.

EXAMPLE 4

The same method as in Example 1 was followed but replacing the aromatic molecule 1.10-phenanthroline-5.6-dione with a molecule of pyrene.

EXAMPLE 5

The same method as in Example 1 was followed but the 1.10-phenanthroline-5.6-dione aromatic molecules were replaced by 9.10-phenanthroline molecules.

EXAMPLE 6

The same method as in Example 1 was followed but the 1.10-phenanthroline-5.6-dione aromatic molecules were replaced by the molecule 5-methyl-1.10-phenanthroline.

EXAMPLE 7

The same method as in Example 1 was followed but the 1.10-phenanthroline-5.6-dione aromatic molecules were replaced by the molecule of 1.4-naphthoquinone.

EXAMPLE 8

The same method as in Example 1 was followed but the 1.10-phenanthroline-5.6-dione aromatic molecules were replaced by the molecule 9.10-phenanthrenequinone.

EXAMPLE 9

The same method as in Example 2 was followed, but the 1.10-phenanthroline-5.6-dione molecules were replaced by 9.10-phenanthroline molecules.

EXAMPLE 10

The same method as in Example 2 was followed, but the 1.10-phenanthroline-5.6-dione molecules were replaced by 5-methyl-1.10-phenanthroline molecules.

COMPARATIVE EXAMPLE 1

A control bioelectrode consisting solely of the film of carbon nanotubes was obtained by preparing a suspension of multi-walled carbon nanotubes at a concentration of 1 mg·mL$^{-1}$ by adding 150 mg of non-functionalized carbon nanotubes (9.5 nm in diameter, purity of more than 95%) in 150 mL of DMF.

This suspension is then shaken manually for one minute.
66 mL of the suspension is filtered through a PTFE millipore filter (JHWP, pore size 0.45 μm, diameter 46 mm) using a vacuum pump (Vacuum$_{max}$=10$^{-3}$ mbar).

The layer of carbon nanotubes was washed with distilled water and allowed to stand for one hour.

After filtration, the resulting "Buckypaper" was allowed to dry at room temperature.

Then the "Buckypaper" obtained is carefully removed from the filter and cut into an electrode of 10 mm diameter (geometric surface 0.785 cm$^2$).

COMPARATIVE EXAMPLE 2

A dispersion of multiwall carbon nanotubes was prepared as in Comparative Example 1 except that the dispersion obtained had a concentration of 2.5 mg·mL$^{-1}$.

Thus, the amount of carbon nanotubes placed in the 2 mL of NMP was not 150 mg but 5 mg.

A drop of a volume of 20 μL of this suspension was then deposited on a glassy carbon support having a surface of 0.196 cm$^2$.

The thickness of the layer of carbon nanotubes obtained was 12±4 μm.

COMPARATIVE EXAMPLE 3

A bioelectrode was prepared following the procedure of Example 2 but stopping before the step of depositing a drop of the 5 mg·mL$^{-1}$ solution of FAD-GDH enzymes.

Thus, the electrode obtained consisted only of carbon nanotubes on which aromatic molecules 1.10-phenanthroline-5.6-dione were absorbed.

COMPARATIVE EXAMPLE 4

A bioelectrode was prepared as in Example 1 except that the adsorption step of the aromatic molecule was not implemented.

A bioelectrode consisting of a support 1 of vitreous carbon coated on one of its faces with a layer 2 of carbon nanotubes on which the FAD-GDH enzymes are directly adsorbed was obtained.

COMPARATIVE EXAMPLE 5

The same method as in Example 1 was followed but the aromatic molecule used was flavin adenine dinucleotide (FAD: cofactor of the enzyme FAD-GDH).

COMPARATIVE EXAMPLE 6

The same method as in Example 1 was followed but the aromatic molecule used was the N-hydroxysuccinimide ester of pyrene butyric acid.

COMPARATIVE EXAMPLE 7

The same method as in Example 2 was followed but the 1.10-phenanthroline-5.6-dione aromatic molecules were replaced by molecules of 1.4-naphthoquinone.

EXAMPLE 11: CHARACTERIZATION CARBON NANOTUBE LAYERS

The characterization of carbon nanotube layers obtained in Comparative Example 1 was carried out with a confocal laser scanning microscope.

The thickness of the carbon nanotube film obtained in Comparative Example 1 was 275±45 μm.

The layer of carbon nanotubes obtained in Comparative Example 1 was characterized with a scanning electron microscope at a magnification of 40,000.

The characterization of the layer of carbon nanotubes obtained in Comparative Example 2 was carried out with a confocal laser scanning microscope.

The thickness of the carbon nanotube film obtained in Comparative Example 2 was 12±4 μm.

The layer of carbon nanotubes obtained in Comparative Example 2 was characterized with a scanning electron microscope at a magnification of 40,000.

It was found that the layer of carbon nanotubes obtained in Comparative Example 1 was denser than the layer of carbon nanotubes obtained in Comparative Example 2, which means that the filtration makes it possible to obtain more compact layers of carbon nanotubes.

The electrode obtained in Comparative Example 7, that is to say a "Buckypaper" consisting of carbon nanotubes on which the 1.10-phenanthroline-5.6-dione mediating aromatic molecules are adsorbed before filtration of nanotube/aromatic molecule mixture, was also studied under a scanning electron microscope at a magnification of 40,000.

This study showed that the aromatic molecule 1.10-phenanthroline-5.6-dione further increases the agglutination of the tubes with each other, as expected, 1.10-phenanthroline-5.6-dione acting as a binder between the carbon nanotubes by exchanging π electrons.

This results in more solid and more flexible "Buckypaper" than the nonfunctional "Buckypaper" given in Comparative Example 1 which are themselves much more fragile.

EXAMPLE 12: ELECTROCHEMICAL CHARACTERIZATION OF THE ELECTRODES OBTAINED IN EXAMPLES 1 TO 8 AND COMPARATIVE EXAMPLES 2, 3, 4 AND 5

Figure 4:
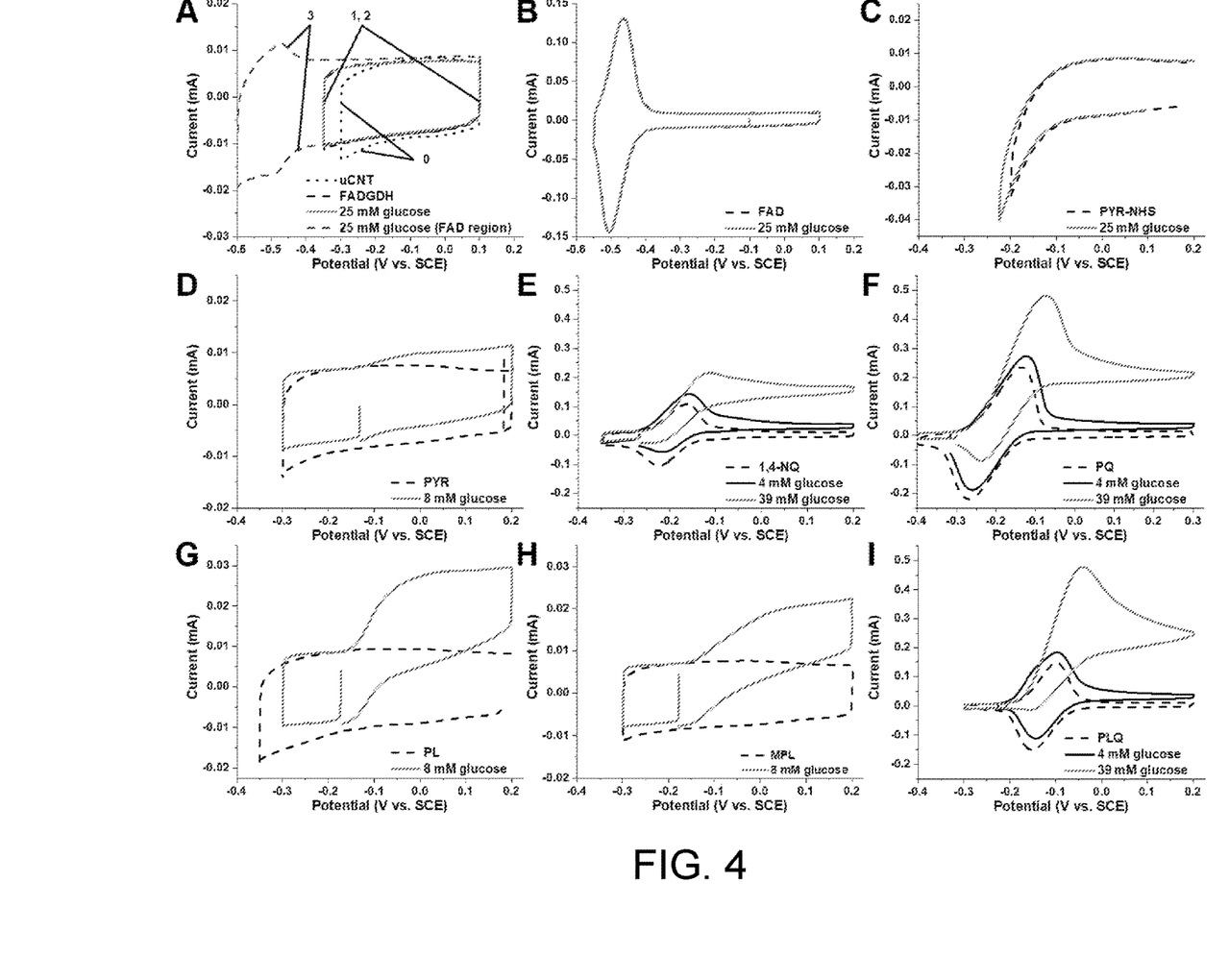
FIG. 4 shows the voltammograms obtained with the electrodes obtained in examples 1, 4 to 8 and Comparative Examples 2 and 4 to 6.

FIG. 4 shows the cyclic voltammograms obtained with each of the electrodes obtained in Examples 1, 4 to 8 and Comparative Examples 2, 4 to 6, as well as the FAD-GDH enzyme alone.

In FIG. 4, the following terms have the following meanings:
uCNT=carbon nanotubes alone,
FADGDH=CNTs functionalized by FAD-GDH,
25 mM glucose=CNTs functionalized by FAD-GDH in the presence of a glucose solution at 25 mmol $L^{-1}$,
25 mM glucose (FAD region)=same as above, including the electroactive region of the FAD-GDH cofactor (FAD) in the measurement window in the presence of a glucose solution at 25 mmol $L^{-1}$,
FAD=Flavin Adenine Dinucleotide,
25 mM glucose=concentration of the glucose solution of 25 mmol $L^{-1}$,
PYR-NHS=N-hydroxysuccinimide ester of pyrene-butyric acid,
PYR=pyrene,
1.4-NQ=1.4-naphthoquinone,
PQ=9.10-phenanthrenequinone,
PL=1.10-phenanthroline,
MPL=5-methyl-1.10-phenanthroline,
PLQ=1.10-phenanthroline-5.6-dione.

The cartridge denoted A in FIG. 4 shows the cyclic voltammograms obtained for the electrodes obtained in Comparative Examples 2 and 4.

The tested electrode was a vitreous carbon electrode (support 1) coated with layer 2 of carbon nanotubes alone (Comparative Example 2) or in which the FAD-GDH enzyme alone was deposited on layer 2 of carbon nanotubes (Comparative Example 4).

It can be seen from the voltammogram shown in cartridge A that there is no visible redox signal (between −0.300 and 0.100 V vs SCE, SCE: reference electrode with saturated calomel [saturated calomel electrode]) on a vitreous carbon electrode covered with a layer 2 of carbon nanotubes (dashed curve 0).

It can also be seen from the voltammogram shown in cartridge A that there is no variation in the catalytic current in the absence or in the presence of glucose for a vitreous carbon electrode covered with a layer 2 of directly modified carbon nanotubes by the layer of FAD-GDH enzymes 4 (the dotted line curve 1 has been obtained in the absence of glucose and the solid line curve denoted 2 is the curve obtained in the presence of glucose, 1 and 2 are perfectly superimposed).

The dashed curve denoted 3 represents the cyclic voltammogram obtained with a larger electrochemical window (from −0.600 to 0.100 V vs SCE), in the presence of a glucose solution at 25 mmol $L^{-1}$.

The curve 3 shows the presence of a redox peak centered on −0.481 V vs. SCE.

This peak is attributed to the electrochemical response of the active center of the FAD-GDH enzyme, FAD, for partially or completely denatured enzymes, which shows that, thanks to its structure, the cofactor of the enzyme can also be adsorbed on the surface of carbon nanotubes. On the other hand, this FAD alone cannot in any case be the seat of an electrocatalytic reaction since the intact structure of the enzyme is a key element of enzymatic catalysis.

This is confirmed by the voltammogram shown in cartridge B of FIG. 4.

This voltammogram was obtained for the electrode obtained in Comparative Example 5 and composed of layers 2, 3 and 4, respectively, of carbon nanotubes, aromatic molecules and FAD enzymes (without or in the presence of glucose at 25 mmol $L^{-1}$, identical curves 1 and 2), with the electrochemical window of −0.600 to 0.100 V vs SCE identical to that used by the curve 3 of cartridge A.

Finding an identical redox potential for the voltammograms of cartridges A and B provides information on the integrity of the enzymes on the electrode.

It is widely reported in the literature that the FAD enzyme, for a functional enzyme, has a higher potential than free FAD in solution.

For this reason, it is reasonable to conclude that the peak present in cartridge A is in fact only free FAD resulting from FAD-GDH whose structure would have been altered and thus inactive enzymes.

FAD alone cannot be enough to oxidize glucose. As such, it is imperative that FAD be inside the protein structure.

In FIG. 4, the cartridge C represents the cyclic voltammograms of the electrode of Comparative Example 6 consisting of a vitreous carbon electrode, of layer 2 of carbon nanotubes functionalized by layer 3 of an aromatic molecule which is 1-pyrenebutyric acid N-hydroxysuccinimide ester (PANHS).

This aromatic molecule is not one of the molecules that can be used in the invention, although the N-hydrosuccinimide ester function is regularly used to carry out peptide-type couplings between a carboxylic acid and an amine function. It should therefore be the N-hydroxysuccinimide function which reacts with the —$NH_2$ functions located on the periphery of the FAD-GDH enzyme and thuscovalently immobilizes this enzyme on the electrode with a totally random orientation. As shown in the voltammogram of the cartridge C, the restriction of movement during the formation of the covalent bond which could have allowed the "key-lock" recognition is no longer feasible.

Cartridges D, G and H represent the cyclic voltammograms of the electrodes obtained in Examples 4, 5 and 6 respectively.

All the aromatic molecules used in these examples are non-electroactive aromatic molecules.

Indeed, no redox signal is observed for such electrodes in the absence of glucose (we find the same signal as for non-functionalized carbon nanotubes) while an electrocatalytic signal is detected during the addition of glucose (solution at 8 mmol $L^{-1}$). This phenomenon can therefore completely resemble direct electron transfer (DET) thanks to the key-lock interaction between the aromatic molecule and the hydrophobic center of the enzyme, which corroborates the fact that 1.10-phenanthroline is an inhibitor of FAD-GDH.

When the aromatic molecule is immobilized on the tubes by π-π interactions, it will tend to attract the active center of the enzyme, without causing its inhibition.

Cartridges E, F and I show the cyclic voltammograms obtained with the electrodes obtained in Examples 7, 8 and 1 respectively.

It can be seen from these cyclic voltammograms that all the quinones show a redox mediator behavior for the mediated electron transfer (MET) of the FAD-GDH enzyme.

Electrocatalytic currents are significantly higher than those obtained by direct electron transfer (DET).

The shape of the cyclic voltammograms, especially for the electrode having the aromatic molecule 1.10-phenanthroline-5.6-dione of Example 1, indicates that a part of the electrocatalytic current could also come from a direct electronic transfer at a low glucose concentration (<4 mmol $L^{-1}$).

1.10-Phenanthroline-5.6-dione therefore appears to be the best redox aromatic molecule for the electrocatalytic oxidation of the FAD-GDH enzyme by using non-covalent immobilization on a layer of carbon nanotubes.

In fact, the electrocatalytic currents measured for the electrodes with aromatic molecules such as 1.4-naphthaquinone aromatic molecules (Example 7) and 9.10-phenanthroquinone (Example 8) do not exceed 200 µA respectively, and 300 µA for potentials higher than 0 V vs SCE, this value of 300 µA is however quite exploitable, after saturation (39 mmol L$^{-1}$ of glucose).

1.10-Phenanthroline-5.6-dione thus has better performances with saturation close to 130 mmol L$^{-1}$ of glucose and currents close to 600-700 µA.

EXAMPLE 13: ELECTROCHEMICAL CHARACTERIZATION OF THE ELECTRODES OBTAINED IN COMPARATIVE EXAMPLE 4

FIG. 5 shows the cyclic voltammograms obtained with each of the electrodes obtained according to Comparative Example 4.

In FIG. 5, the following terms have the following meanings:

0 µM PX=CNTs functionalized by FAD-GDH in the presence of a glucose solution at 100 mmol L$^{-1}$ and in the absence of any aromatic molecules (X representing the aromatic molecule PLQ (cartridge A) or PQ (cartridge B))

400 µM PX=CNTs functionalized by FAD-GDH in the presence of a glucose solution at 100 mmol L$^{-1}$ and 400 µmol L$^{-1}$ of an aromatic molecule PLQ (cartridge A) or PQ (cartridge B)

400 µM PX (180 min)=CNTs functionalized by FAD-GDH in the presence of a glucose solution at 100 mmol L$^{-1}$ and 200 µmol L$^{-1}$ of an aromatic molecule PLQ (cartridge A) or PQ (cartridge B) after incubation in the solution with a duration of 180 minutes.

200 µM PQ=CNTs functionalized by FAD-GDH in the presence of a solution of glucose at 100 mmol L$^{-1}$ and 200 µmol L$^{-1}$ of an aromatic molecule PQ (cartridge C and D)

200 µM PQ+200 µM PY (180 min)=CNTs functionalized by FAD-GDH in the presence of a glucose solution at 100 mmol L$^{-1}$, 200 µmol L$^{-1}$ of an aromatic molecule PQ and 200 µmol L$^{-1}$ of an aromatic molecule PY after incubation in the solution for a duration of 180 minutes. (Y represents the aromatic molecule PL (cartridge C) or PH (cartridge D)).

PLQ=1.10-phenanthroline-5.6-dione.
PQ=9.10-phenanthrenequinone,
PL=1.10-phenanthroline,
PH=phenanthrene, The cartridge denoted A in FIG. 5 shows the cyclic voltammograms obtained for the electrodes obtained in Comparative Example 4.

The electrode tested was a vitreous carbon electrode (support 1) in which the FAD-GDH enzyme alone was deposited on layer 2 of carbon nanotubes (Comparative Example 4).

From the voltammogram shown in cartridge A, there is a strong increase in the catalytic current between −0.250 and 0.150 V vs SCE on a vitreous carbon electrode in which the FAD-GDH enzyme alone has been deposited on layer 2 of carbon nanotubes since PLQ is present (black solid line) opposite to the absence of redox mediator in solution (black dashed line).

It can also be seen from the voltammogram shown in cartridge A that there is a sharp decrease in the catalytic current after 180 minutes of immersion of the electrode in the solution containing 100 mmol L$^1$ of glucose and 400 µmol L$^{-1}$ of PLQ. for the same vitreous carbon electrode covered with a layer 2 of carbon nanotubes modified directly by layer 4 of FAD-GDH enzyme. This suggests a progressive inhibition of the enzyme by PLQ (electroactive analogue of PL, inhibitor cited by the company supplying the enzyme).

In the same way, a strong increase of the catalytic current between −0.300 and 0.150 V vs SCE is noticed in cartridge B, C and D on a vitreous carbon electrode in which the FAD-GDH enzyme only was deposited on layer 2 of carbon nanotubes when PQ is present (black solid line) opposite to the absence of redox mediator in solution (black dashed line).

On the other hand, in this case, no decrease in the catalytic current is observed after a 180 min incubation of the electrode described above in a solution containing 100 mmol L$^1$ of glucose and 400 µmol L$^{-1}$ of PQ.

This observation remains valid when the solution consists of 100 mmol L$^1$ of glucose and 200 µmol L$^{-1}$ of PQ and 200 µmol L$^{-1}$ of PH (non-electroactive analogue of PQ).

The phenomenon is reversed when the solution consists of 100 mmol L$^{-1}$ of glucose and 200 µmol L$^{-1}$ of PQ and 200 µmol L$^{-1}$ of PL. The catalytic current drops again and the inhibition phenomenon described by the manufacturer of the FAD-GDH is obtained.

The invention claimed is:

1. A bioelectrode, comprising the superposition of:
   a layer (2) of carbon nanotubes,
   a layer (3) deposited on the layer (2) of carbon nanotubes, consisting of aromatic molecules chosen from the group formed by 9.10-phenanthrenequinone, 1.10-phenanthroline-5.6-dione, 9.10-anthraquinone, phenanthrene, 1.10-phenanthroline, 5-methyl-1.10-phenanthroline, pyrene, 1-aminopyrene, pyrene-1-butyric acid, and mixtures of two or more of these molecules, and
   a layer (4) of Flavin Adenine Dinucleotide-Glucose Dehydrogenase (FAD-GDH) enzymes adsorbed on the layer (3) of the aromatic molecules, wherein said FAD is inside said GDH.

2. The bioelectrode according to claim 1, further comprising a layer (6) of a porous and optionally hydrophilic material covering at least the free surface of the layer (4) of FAD-GDH enzymes.

3. The bioelectrode according to claim 1, wherein the layer (4) consists of 9.10-phenanthrenequinone or 1.10-phenanthroline-5.6-dione molecules.

4. The bioelectrode according to claim 1, wherein the layer (2) of carbon nanotubes consists of between 2.5 µg and 510 µg of carbon nanotubes per cm$^2$ of layer surface.

5. The bioelectrode of claim 1, wherein the support (1) is made of an electron-conducting material.

6. The bioelectrode of claim 1, wherein a wire made of an electrically conductive material is connected to the surface of the layer (2) of carbon nanotubes which is not covered by the layer (3) of aromatic molecules.

7. The bioelectrode of claim 1, further comprising a layer (5) of coating impervious to fluids, that surrounds the superposition of the layers (2), (3) and (4).

8. A device comprising the bioelectrode of claim 1.

9. The device of claim 8, wherein the device is a biofuel enzymatic cell.

10. A device comprising the bioelectrode of claim 1, wherein the device is a device for detecting glucose.

11. A method for the oxidation of glucose, comprising using the bioelectrode of claim 1 to oxidize glucose.

12. A method for producing the bioelectrode of claim 1, consisting of the following steps:
   a) preparing a suspension of carbon nanotubes having a concentration of carbon nanotubes of between 0.5 mg·mL$^{-1}$, and 10 mg·mL$^{-1}$, in an organic solvent selected from N-methyl-2-pyrrolidone (NMP), dichloromethane (DCM), acetonitrile (ACN), 1.3-dioxolane (DXL), dimethylformamide (DMF), and mixtures of two or more of these molecules, b) depositing a drop-casting of the suspension of carbon nanotubes obtained in step a) on a support (1) made of an electron-conducting material, c) evaporation of the organic solvent from the suspension of carbon nanotubes, whereby a layer (2) of carbon nanotubes is formed on the support (1), d) preparing a solution comprising aromatic molecules, selected from the group consisting of 9.10-phenanthrenequinone, 1.10-phenanthroline-5.6-dione, 9.10-anthraquinone, phenanthrene, 1.10-phenanthroline, 5-methyl-1.10-phenanthroline, pyrene, 1-aminopyrene, pyrene-1-butyric acid, and mixtures of two or more molecules, having a concentration including between 0.5 mmol·L$^{-1}$ and 15 mmol·L$^{-1}$ of aromatic molecules dissolved in an organic solvent identical to or different from the organic solvent of the suspension of carbon nanotubes the solvent being selected from NMP, DCM, ACN, DXL, DMF and mixtures of two or more thereof, e) depositing on a surface of the layer (2) of carbon nanotubes obtained in step c) of the solution of aromatic molecules obtained in step d), by deposition of a drop of the solution of aromatic molecules on the surface of the layer (2), or by incubation of at least the free surface of the layer (2) in the solution aromatic molecules obtained in step d), f) evaporation of the solvent from the solution of aromatic molecules deposited in step e), whereby a layer (3) of aromatic molecules is formed on the layer (2), g) preparation of an aqueous solution of FAD-GDH enzymes having a FAD-GDH enzyme concentration of between 0.1 mg·mL$^{-1}$ and 5 mg·mL$^{-1}$, h) depositing on the layer (3) of aromatic molecules obtained in step f), the FAD-GDH enzyme solution obtained in step g), by incubation of at least the free surface of the layer (3) aromatic molecules in an aqueous solution containing the FAD-GDH enzymes obtained in step g), or by depositing a drop-casting of said aqueous solution containing the FAD-GDH enzymes obtained in step f) on the free surface of the layer (3).

13. The method of claim 12, wherein step a) of depositing a drop of the dispersion of carbon nanotubes is repeated at least once.

14. The method of claim 12, further comprising a step for depositing a layer (6) of a porous material on at least the surface free of the layer (4).

15. The method of claim 12, further comprising a step of deposition of a coating to the superposition: layer (2) of carbon nanotubes/layer (3) aromatic molecules/layer (4) of FAD-GDH enzymes/optionally support (1)/wire made of an electrically conductive material, wherein the coating is a material impervious to fluids.

16. A method for producing the bioelectrode of claim 1, consisting of the following steps:

A) preparing a suspension of carbon nanotubes in an organic solvent with a suspension having a concentration of carbon nanotubes of between 1 mg·mL$^{-1}$ and 15 mg·mL$^{-1}$, B) preparation of a solution of aromatic molecules selected from the group consisting of 9.10-phenanthrenequinone, 1.10-phenanthroline-5.6-dione, 9.10-anthraquinone, phenanthrene, 1.10-phenanthroline, 5-methyl-1.10-phenanthroline, pyrene, 1-aminopyrene, 1-pyrene-butyric acid, and mixtures of two or more elements, in an organic solvent selected from NMP, DCM, ACN, DXL, DMF and mixtures of two or more elements of the same or different from the organic solvent of the suspension of carbon nanotubes obtained in step a), this solution of aromatic molecules having a concentration of aromatic molecules of between 0.5 mmol·L$^{-1}$ and 15 mmol·L$^{31\ 1}$, C) addition of the solution of aromatic molecules obtained in step b) in the suspension of nanotubes obtained in step A), and mixing, D) filtering the dispersion obtained in step C) through a filter support, E) evaporation of the solvent from the suspension of carbon nanotubes and the solvent of the solution of aromatic mediator molecules, whereby a layer (2) of carbon nanotubes, itself covered on at least one of its surfaces with a layer (3) of said aromatic molecules are formed, F) preparation of an aqueous solution of FAD-GDH enzymes having a concentration of FAD-GDH enzymes of between 0.1 and 5 mg·mL$^{-1}$, G) depositing a drop of 150 µl of the FAD-GDH enzyme solution prepared in step F) on the free surface of the layer (3) thus forming a layer (4) of adsorbed FAD-GDH enzymes on the layer (3) of aromatic molecules, and H) removal of the assembly obtained in step G of the filter support.

17. The method of claim 16, further comprising a step k1) of fixing a wire of an electrically conductive material on the surface of the layer (2) of nanotubes of carbon not covered with the layer (3) of aromatic molecules, wherein the step k1) is implemented before or after step G) of deposition of the layer (4) of FAD-GDH enzymes.

18. A method for producing the bioelectrode of claim 1, consisting of the following steps:

a1) preparing a suspension of carbon nanotubes in an organic solvent, having a concentration of carbon nanotubes of between 1 mg·mL$^{-1}$ and 15 mg·mL$^{-1}$, b1) preparation of a solution of aromatic molecules selected from the group consisting of 9.10-phenanthrenequinone, 1.10-phenanthroline-5.6-dione, 9.10-anthraquinone, phenanthrene, 1.10-phenanthroline, 5-methyl-1.10-phenanthroline, pyrene, 1-aminopyrene, 1-pyrene-butyric acid, and mixtures of two or more molecules, in an organic solvent identical or different from the organic solvent of the suspension of carbon nanotubes obtained in step a1), this solution having an aromatic molecule concentration of between 0.5 and 15 mmol·L$^{-1}$, c1) filtering the dispersion obtained in step b1) through a filter support (1), d1) evaporation of the solvent from the dispersion of carbon nanotubes deposited in step c), whereby a layer (2) of carbon nanotubes is formed, e1) removing the layer of carbon nanotubes obtained in step d1) from the filter support (1), f1) depositing a drop of 150 µl of the aromatic molecule solution obtained in step b1) on at least one surface of the layer (2) of carbon nanotubes obtained in step e1), g1) evaporation of the solvent from the solution of aromatic molecules deposited in step f1), whereby a layer (3) of said aromatic molecules is formed on the layer (2) of carbon nanotubes, h1) preparation of an aqueous solution of FAD-GDH enzymes, having a concentration of FAD-GDH enzymes of between 0.1 and 5 mg·mL$^{-1}$, and i1) depositing a drop of 150 µl of the FAD-GDH enzyme solution obtained in step h) on at least one surface of the layer (3) of aromatic molecules, thus forming a layer (4) of FAD-GDH enzymes adsorbed on the layer (3).

19. The method of claim 18, further comprising a step k1) of fixing a wire of an electrically conductive material on the surface of the layer (2) of nanotubes of carbon not covered with the layer (3) of aromatic molecules, wherein the step k1) is implemented before or after step i1) of deposition of the layer (4) of FAD-GDH enzymes.

\* \* \* \* \*